United States Patent [19]

Rajan

[11] Patent Number: 4,547,603
[45] Date of Patent: Oct. 15, 1985

[54] METHYLCYCLOPENTADIENE SYNTHESIS

[75] Inventor: Sundar J. Rajan, Ferndale, Mich.

[73] Assignee: Ethyl Corporation, Richmond, Va.

[21] Appl. No.: 371,286

[22] Filed: Apr. 23, 1982

[51] Int. Cl.$^4$ ................................. C07C 5/40
[52] U.S. Cl. .................................. 585/375; 585/317; 585/376
[58] Field of Search ................. 585/317, 318, 375

[56] References Cited

U.S. PATENT DOCUMENTS 2,916,504  12/1959  Shapiro .......................... 260/429
2,964,547  12/1960  De Witt et al. ................. 260/429

OTHER PUBLICATIONS

McLean et al., Can. J. Chem., 41, 1231, (1963) (I).
Mironov et al., Tetrahedron, 19, 1939, (1963).
McLean et al., Tetrahedron, 21, 2313, (1965) (II).

Primary Examiner—W. J. Shine
Assistant Examiner—A. Pal
Attorney, Agent, or Firm—Donald L. Johnson; John F. Sieberth; John F. Hunt

[57] ABSTRACT

Synthesis of methylcyclopentadiene with limited amounts of dimethylcyclopentadiene by-product. Cyclopentadiene monomer is complexed with metallic sodium in diglyme (diethylene glycol dimethylether) and reacted with an alkylating agent such as methyl chloride in the presence of a large stoichiometric excess of cyclopentadiene monomer. A high yield of methylcyclopentadiene is obtained with only a small production of undesirable methylcyclopentadiene. The excess cyclopentadiene is easily recycled in a continuous process.

17 Claims, No Drawings

METHYLCYCLOPENTADIENE SYNTHESIS

BACKGROUND OF THE INVENTION

1. Field of the Invention

This invention relates to alkylating syntheses and gasoline additives in general. This invention also relates to the favorable production of alkylcyclopentadienes with minimal production of di- and polyalkylated cyclopentadiene by-products.

2. Description of the Prior Art

Methylcyclopentadiene manganese tricarbonyl (MMT) is a valuable additive for leaded gasoline and may find use in other fuels. The use of other alkyl homologs of MMT in fuels is also indicated.

The successful production of MMT depends upon a reliable source of methylcyclopentadiene unmixed with higher alkylated by-products. The methylcyclopentadiene starting material has been available in suitable purity by obtaining it from a petroleum cracking process where undesirable portions of the di- or polyalkylated cyclopentadienes are not formed. However, the amount of methylcyclopentadiene available is limited to a single source and an alternative source is desirable.

Both McLean et al, Tetrahedron, 21, 2313 (1965) and Mironov et al, Tetrahedron, 19, 1939 (1963) report the synthesis of methylcyclopentadiene with the attendant production of large portions of di- and polymethylated cyclopentadienes. Synthesis may form dimethyl-, trimethyl-, or even tetramethylcyclopentadiene. The higher alkylated cyclopentadienes are present in an amount of about 10 mole percent or more which is unacceptable for two reasons. The dimethylcyclopentadiene is separated from the methylcyclopentadiene product only by means of a difficult distillation. Also, the higher alkylated cyclopentadienes interfere with the production of MMT.

SUMMARY OF THE INVENTION

The present invention is directed to providing an alternative source of monoalkylcyclopentadiene having a minimal amount of dialkyl or polyalkylcyclopentadienes mixed therewith as by-products. Methylcyclopentadiene is the precursor to the commercially important gasoline antiknock additive, methylcyclopentadiene manganese tricarbonyl (MMT). Preparation of MMT and similar compounds may be suitably accomplished in accordance with the methods described in U.S. Pat. No. 2,916,504 and U.S. Pat. No. 2,964,547, for example.

The present invention is a process for limiting the formation of di- and polyalkylcyclopentadiene by-products in the synthesis of monoalkylcyclopentadiene, said process comprising the steps of:

(a) complexing cyclopentadiene monomer with sodium;

(b) reacting an alkylating agent with the cyclopentadiene sodium complex so formed, in the presence of a large stoichiometric excess of cyclopentadiene monomer to form the corresponding monoalkylcyclopentadiene, and (c) recovering the monoalkylcyclopentadiene.

The present invention is also a cyclic continuous process for limiting by-product formation of di- and polyalkylcyclopentadiene in the production of monoalkylcyclopentadiene, said process comprising:

(a) continually reacting a large stoichiometric excess of cyclopentadiene monomer with metallic sodium in a stabilizing medium at above the melting point of sodium to form a sodium cyclopentadiene complex;

(b) adding alkylating agent to the sodium cyclopentadiene complex in the presence of the excess cyclopentadiene monomer so as to form the corresponding monoalkylcyclopentadiene;

(c) recovering the so formed monoalkylcyclopentadiene; and (d) recycling excess unreacted cyclopentadiene.

Monoalkylcyclopentadienes may be synthesized according to the invention as follows:

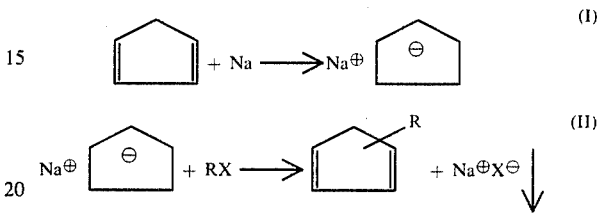

where RX is an alkylating agent.

Suitable alkylating agents include the lower alkyl halides such as methyl chloride, methy bromide, ethyl bromide, methyl iodide, and the like.

Also suitable are agents such as dimethyl sulfate. Methyl chloride is especially preferred since it gives good conversions based on the methyl group and provides the valuable intermediate methylcyclopentadiene. Also, methyl chloride is a gas and therefore more easily handled on a commercial scale.

Preparation of alkylcyclopentadienes in accordance with reactions (I) and (II) may provide yields of the monoalkylcyclopentadiene of nearly 80 percent. Unfortunately, by the methods of the prior art these yields are contaminated with 10-15 percent or more di- and polyalkylated cyclopentadienes which seriously devalue the product.

While Applicant does not wish to be bound by the theory explained below, this theory may serve to explain the success achieved by the invention. The following equilibrium appears to exist:

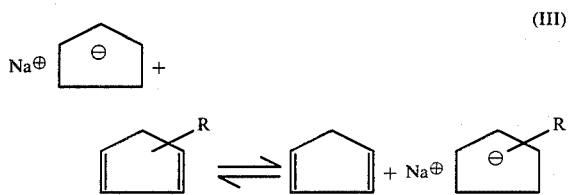

Of course the ionic species on the right-hand side of equilibrium (III) could readily lead to the formation of di- or polyalkylcyclopentadienes as follows:

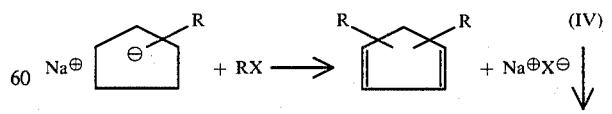

According to the invention reaction (II) is carried out in the presence of a large excess of cyclopentadiene monomer. I have found that the production of di- and polyalkylcyclopentadiene by reaction (IV) is minimized since excess cyclopentadiene drives equilibrium (III) to the left.

DESCRIPTION OF THE PREFERRED EMBODIMENTS

The following examples demonstrate the best mode of the invention of which I am now aware. Example 1 uses a 25 percent excess of cyclopentadiene. Example 2 uses a 100 percent excess of cyclopentadiene to realize even lower by-product amounts of dialkylcyclopentadiene.

EXAMPLE 1

Due to the character of sodium metal and the instability of cyclopentadiene monomer at room temperature, the reactants must be prepared as follows.

Dicyclopentadiene was cracked at 160° C. and stored over dry ice until used.

Bis(2-methoxyethyl)ether, also known as diglyme, serves as a suitable stabilizing medium for the sodium metal. The ether was stirred over a 13× molecular sieve for two hours and distilled over sodium before use.

All glassware was oven dried, assembled, and continually nitrogen flushed until use. A high speed stirrer (20,000 rpm) was used for sodium dispersion in the ether (diglyme).

Tetrahydrofuran (THF) would also be a suitable solvent for alkylation of the sodium-complexed cyclopentadiene if the sodium dispersion is first prepared in a higher boiling solvent such as xylene. Alternatively, ethylene glycol dimethyl ether, monoglyme, could be used for the alkylation reaction.

Sodium, 8.94 grams (0.39 gram-atom) was added to 210 ml bis(2-methoxyethyl)ether at ambient temperature in a nitrogen flushed, three-neck flask equipped with stirrer and condenser. The mixture was heated to 98°–105° C. to melt and disperse the sodium. To this dispersion 40 ml (0.48 mole) cyclopentadiene was added over a period of about 20 minutes. The mixture was purple in color. All of the sodium had dissolved after another 20 minutes. The reaction mixture was then cooled to about 26° C.

About 35 grams (0.69 mole) methyl chloride was bubbled into the sodium/cyclopentadiene complex solution over a period of about 40 minutes. The product was analyzed by gas chromatography and structures were confirmed by mass spectrometry. The product analysis is given in the Table following Example 2.

EXAMPLE 2

Generally the same procedure was followed as for Example 1 above. About 64 ml (0.78 mole) cyclopentadiene was added over a period of 45 minutes to a dispersion of 8.94 grams (0.39 gram-atom) sodium metal melted in diglyme at about 100°–110° C. The mixture was stirred an additional 15 minutes before adding 40 grams (0.8 mole) methyl chloride at 18°–32° C. over a period of 90 minutes. The reaction mixture was then stirred an additional 30 minutes and stored overnight before analysis by gas chromatography and mass spectrometry.

The 25 percent and 100 percent stoichiometric excess cyclopentadiene of Examples 1 and 2, respectively, were factored out before calculation of the yields given in the Table below.

TABLE

| | Component | Product Yield Mole Percent 1 | 2 |
|---|---|---|---|
| A | Cyclopentadiene (CP) | 6.2 | — |
| | Cyclopentadiene dimer-CP/CP | 6.5 | 5.0 |
| B | Methylcyclopentadiene (MCP) | 70.7 | 83.9 |
| | MCP/MCP (dimer) | 5.8 | 2.4 |
| | CP/MCP | 4.3 | 6.4 |
| C | Dimethylcyclopentadiene (DMCP) | 6.2 | 2.4 |
| | MCP/DMCP | 0.25 | — |

The components in group A of the Table are reuseable along with the excess cyclopentadiene used for the reaction. Of course the cyclopentadiene dimer must first be cracked to monomer at about 160° C. as noted above. The methylcyclopentadiene dimer and the CP/MCP components of group B in the Table may be cracked to provide additional product and recyclable cyclopentadiene.

The group C components are admixed with the product methylcyclopentadiene in only such relatively small amounts as do not inhibit the synthesis of methylcyclopentadiene manganese tricarbonyl.

The process of the invention is especially advantageous because excess cyclopentadiene may be conveniently recycled in a continuous process where a product stream of methylcyclopentadiene is withdrawn in a conventional manner.

While particular non-limiting variations of the invention are presented above, certain aspects of the invention such as stabilizing medium and alkylating agent may be varied without departing from the scope or spirit of the invention as defined by the appended claims.

I claim:

1. A process for limiting the formation of di- and polyalkylcyclopentadiene by-products in the synthesis of monoalkylcyclopentadiene, said process comprising the steps of:
   (a) complexing cyclopentadiene monomer with sodium;
   (b) reacting an alkylating agent with the cyclopentadiene sodium complex so formed, in the presence of a large stoichiometric excess of cyclopentadiene monomer to form the corresponding monoalkylcyclopentadiene, and
   (c) recovering the monoalkylcyclopentadiene.

2. The process of claim 1 wherein the alkylating agent is selected from the group consisting of methyl chloride, methyl bromide, ethyl bromide, methyl iodide, and dimethyl sulfate.

3. The process of claim 2 wherein said alkylating agent is methyl chloride.

4. The process of claim 1 wherein the cyclopentadiene monomer is complexed with sodium at a temperature above the melting point of sodium and in a stabilizing medium.

5. The process of claim 4 wherein said stabilizing medium is an ethylene glycol dimethylether.

6. The process of claim 5 wherein the ether is $(CH_3-O-CH_2CH_2)_2O$.

7. The process of claim 1 wherein the large stoichiometric excess of cyclopentadiene monomer is present in a ratio of at least about 1.25 mole parts per gram-atom part of sodium.

8. The process of claim 7 wherein the excess is at least about two mole parts per gram-atom part of sodium.

9. The process of claim 1 wherein the alkylating agent is reacted with the cyclopentadiene sodium complex at about ambient temperature.

10. A cyclic continuous process for limiting by-product formation of di- and polyalkylcyclopentadiene in the production of monoalkylcyclopentadiene, said process comprising:
   (a) continually reacting a large stoichiometric excess of cyclopentadiene monomer with metallic sodium in a stabilizing medium at above the melting point of sodium to form a sodium cyclopentadiene complex;
   (b) adding alkylating agent to the sodium cyclopentadiene complex in the presence of the excess cyclopentadiene monomer so as to form the corresponding monoalkylcyclopentadiene;
   (c) recovering the so formed monoalkylcyclopentadiene; and
   (d) recycling excess unreacted cyclopentadiene.

11. The process of claim 10 wherein metallic sodium is provided in a stabilizing medium of bis(2-methoxyethyl)ether.

12. The process of claim 10 wherein the alkylating agent is selected from methyl chloride, methyl bromide, methyl iodide, and dimethyl sulfate.

13. The process of claim 12 wherein the alkylating agent is methyl chloride.

14. The cyclic process of claim 10 wherein at least about 1.25 mole parts cyclopentadiene are continually provided for reaction with each gram-atom part of sodium.

15. A process for limiting the by-product formation of dimethyl- and polymethylcyclopentadiene in the production of methylcyclopentadiene, said process comprising the steps of:
   (a) mixing a large stoichiometric excess of cyclopentadiene monomer with a dispersion of sodium;
   (b) adding methyl halide to the mixture of (a) to form methylcyclopentadiene; and
   (c) recovering said methylcyclopentadiene.

16. The process of claim 15 wherein the large stoichiometric excess is at least about 1.25 mole parts cyclopentadiene per gram-atom part sodium.

17. The process of claim 16 wherein said methyl halide is methyl chloride.

* * * * *